United States Patent
Tankovich

[19]
[11] Patent Number: 5,871,480
[45] Date of Patent: *Feb. 16, 1999

[54] HAIR REMOVAL USING PHOTOSENSITIZER AND LASER

[75] Inventor: Nikolai I. Tankovich, San Diego, Calif.

[73] Assignee: ThermoLase Corporation, San Diego, Calif.

[*] Notice: The term of this patent shall not extend beyond the expiration date of Pat. No. 5,425,728.

[21] Appl. No.: 900,178

[22] Filed: Jul. 25, 1997

Related U.S. Application Data

[60] Continuation-in-part of Ser. No. 471,141, Jun. 6, 1995, abandoned, which is a division of Ser. No. 5,810, Jan. 19, 1993, Pat. No. 5,425,728, which is a continuation of Ser. No. 783,789, Oct. 29, 1991, Pat. No. 5,226,907.

[51] Int. Cl.⁶ .......................... A61B 17/36; A61B 17/50
[52] U.S. Cl. ................................... 606/9; 606/131
[58] Field of Search .................. 606/1, 9, 2, 131, 606/133, 36, 43; 128/898

[56] References Cited

U.S. PATENT DOCUMENTS

| | | |
|---|---|---|
| 3,538,919 | 11/1970 | Mayer . |
| 3,693,623 | 9/1972 | Harte et al. . |
| 3,769,963 | 11/1973 | Goldman et al. . |
| 3,794,028 | 2/1974 | Mueller et al. . |
| 3,834,391 | 9/1974 | Block . |
| 3,900,034 | 8/1975 | Katz et al. . |
| 4,336,809 | 6/1982 | Clark . |
| 4,388,924 | 6/1983 | Weissman et al. . |
| 4,461,294 | 7/1984 | Baron . |
| 4,608,978 | 9/1986 | Rohr . |
| 4,617,926 | 10/1986 | Sutton . |
| 4,712,543 | 12/1987 | Baron . |
| 4,813,412 | 3/1989 | Yamazaki . |
| 5,059,192 | 10/1991 | Zaias . |
| 5,425,728 | 6/1995 | Tankovich ................................ 606/9 |

FOREIGN PATENT DOCUMENTS

| | | |
|---|---|---|
| 10416-10 | 6/1974 | Canada . |
| 1208702 | 7/1986 | Canada . |
| D64967A2 | 4/1995 | European Pat. Off. . |
| 2267122 | 11/1975 | France . |
| 25907-91 | 6/1987 | France . |
| 2595239 | 9/1987 | France . |
| 2515697 | 10/1975 | Germany . |
| 3220962 | 12/1983 | Germany . |
| 63-249577 | 10/1988 | Japan . |
| 8002640 | 12/1980 | WIPO . |
| 8602783 | 5/1986 | WIPO . |
| WO 90/11653 | 10/1990 | WIPO . |
| 9104073 | 4/1991 | WIPO . |
| WO 91/13653 | 9/1991 | WIPO . |
| WO 93/21842 | 11/1993 | WIPO . |
| WO 93/21992 | 11/1993 | WIPO . |

OTHER PUBLICATIONS

Porphyrins in Tumor Phototherapy—Andereoni May 16, 1983 1984–pp. 143–155.

Investigation and Therapy in Dermatology A. Anders, et al—Conf. Laser 77 Optics–Electronics (20–24 Jun. 1977).

*Primary Examiner*—Glenn K. Dawson
*Attorney, Agent, or Firm*—Fish & Richardson P.C.

[57] ABSTRACT

A device and process for the permanent removal of unwanted human hair. Hair on a section of skin is contaminated with a substance having high absorption of a frequency band of light. The skin is illuminated with light at this frequency band at sufficient intensity and duration to kill the follicles or the skin tissue feeding the hair. Specific embodiments to produce death of the follicles or the skin tissues feeding the hair by heating and by photochemical reaction.

17 Claims, 5 Drawing Sheets

HAIR REMOVAL USING PHOTOSENSITIZER AND LASER

This application is a continuation in part application of U.S. patent application Ser. No. 08/471,141, filed Jun. 6, 1995, now abandoned, which is a division of U.S. patent application Ser. No. 08/005,810, filed Jan. 19, 1993, now issued U.S. Pat. No. 5,425,728, which is a continuation application of U.S. patent application Ser. No. 07/783,789, filed Oct. 29, 1991, now issued U.S. Pat. No. 5,226,907.

BACKGROUND

1. Technical Field

This invention relates to devices and methods for hair removal, and, in particular, to the use of laser devices for inhibition of hair regrowth.

2. Background Information

The principal methods presently used for hair removal involve the use of electrolysis techniques or chemical depilatories. These techniques involve some pain, are time consuming, and demand a fair degree of expertise in their application. Normally do not guarantee a permanent effect.

Laser use in medicine is well known. For example, lasers are used in surgery for both cutting and cauterization. Lasers have been used for many years for removing tattoos under the surface of the skin. In this case a laser beam penetrates the skin and is absorbed by and destroys the ink particle. A similar procedure has been used for years to remove birth marks where the laser is matched to an absorption peak of the hemoglobin in erythrocytes in the tiny capillaries under the skin to destroy the capillaries.

The prior art of hair removal also includes attempts at removing hair with laser beams. Three such techniques are described in the following United States patents: Weissman et al., "Method for Laser Depilation," U.S. Pat. No. 4,388,924; Sutton, "Depilation Device and Method," U.S. Pat. No. 4,617,926; and Mayer, "Depilation by Means of Laser Energy," U.S. Pat. No. 3,538,919. All of these devices and methods teach the removal of hairs one hair at a time with a narrowly focused laser beam. Therefore, they are relatively inefficient and time consuming. A patent by Zaias, U.S. Pat. No. 5,059,192, issued Oct. 22, 1991, discloses a process for using a laser beam matched to the melanin found at the base of the hair follicle and papilla.

It has been known for at least 20 years in the medical profession that selective absorption of laser radiation can sometimes be enhanced by the technique of staining pathological tissues with various vital dyes. (See Goldman, U.S. Pat. No. 3,769,963.)

What is needed is a simple, harmless method for removal of and/or inhibiting growth of hair over a relatively broad area of skin.

SUMMARY

The present invention provides a process for long term inhibition of growth of unwanted human hair. The hair or the skin tissue feeding or surrounding the hair on a section of skin is contaminated with a photosensitizer having high absorption of a frequency band of light. The section of skin containing the contaminated follicles is illuminated with light at the highly absorbed frequency band at sufficient intensity and duration to photoactivate the photosensitizer, thereby producing a chemical species that damages the follicle and/or skin tissue feeding the hair so as to cause long term inhibition of hair growth from the follicle.

In one embodiment of the process for inhibiting growth of hairs in a hair duct, a photosensitizer having a high absorption at at least one frequency band of light is applied topically to the section of skin to be treated. Upon application, the photosensitizer penetrates into the hair duct, for example by capillary action. The skin surface can also be massaged to facilitate penetration of the photosensitizer, and then the surface of the skin is usually cleaned off, for instance with an alcohol-soaked pad.

Upon penetration, the photosensitizer is preferentially, rapidly absorbed into cells within the hair duct and adjacent tissue structures that generate hair growth. For example, such cells include hair papilla cells, stem cells, and keratiocytes, due to the extremely high metabolic rate of these cells, and endothelial blood vessels. Absorption of the photosensitizer into other, more slowly growing cells, is at a substantially slower rate. Therefore, photoactivation of the photosensitizer in the hair duct with a frequency-matched light is timed to commence after at least a portion of the photosensitizer is absorbed into the cells that produce hair, but before substantial absorption of the photosensitizer into cells on the skin surface, or at a distance of more than about 100 $\mu$m from the surface of the hair duct takes place. For example, when a 20% by weight solution of a hematoporphyrin derivative is applied topically to skin in pure or liposomal formulation, the frequency-matched laser can be an argon dye laser having a wavelength of about 632 nm., and the illumination can commence within about 20 minutes to about 20 hours of application. By timing the illumination in this manner, the hair-producing cells in the follicle, as well as the tissue immediately surrounding the follicle that feed the hair, are damaged upon photochemical activation of the photosensitizer, but without substantial damage to other tissue.

This method provides the advantage that it is not necessary to wait for many hours between application of the photosensitizer and illumination by the frequency-matched light. In many cases the whole treatment process can be completed within a single treatment session requiring as little time as one to four hours.

In additional embodiments of the process for inhibiting growth of hairs, a biocompatible photosensitizer is administered orally or intravenously, and delivered to the hair follicles by metabolic processes. Illumination of the skin surface with frequency-matched light commences once the photosensitizer has been delivered to the hair follicles by metabolic processes, which generally requires no more than a few hours. For example, oral administration of a solution of disodium fluorescein at a concentration of about 2% to about 10% by weight will be preferentially distributed to the hair follicles by metabolic processes within about 3 to about 6 hours. Therefore, when a solution of disodium fluorescein in this concentration range is ingested, illumination of the skin section to be treated with frequency-matched light will commence within about 3 to 6 hours following ingestion of the photosensitizer. Examples of frequency-matched light sources for use with disodium fluorescein are a He—Cd or Nd:YAG doubled frequency laser, for instance within about 20 minutes to 20 hours of application. For example, long term inhibition of hair growth from the hair follicles illuminated by the laser is achieved without substantial damage to other hair follicles, or to skin tissue other than that in and immediately surrounding the hair follicles illuminated by the frequency-matched light.

DESCRIPTION OF DRAWINGS

FIGS. 2 A, B and C show a cross section of skin and three hairs during three stages of a process of one embodiment of the present invention.

Like reference numbers and designations in the various drawings indicate like elements.

DETAILED DESCRIPTION

Preferred embodiments of the present invention can be described by reference to the figures.

COAT AND HEAT METHOD

Skin Preparation

Figure 1:
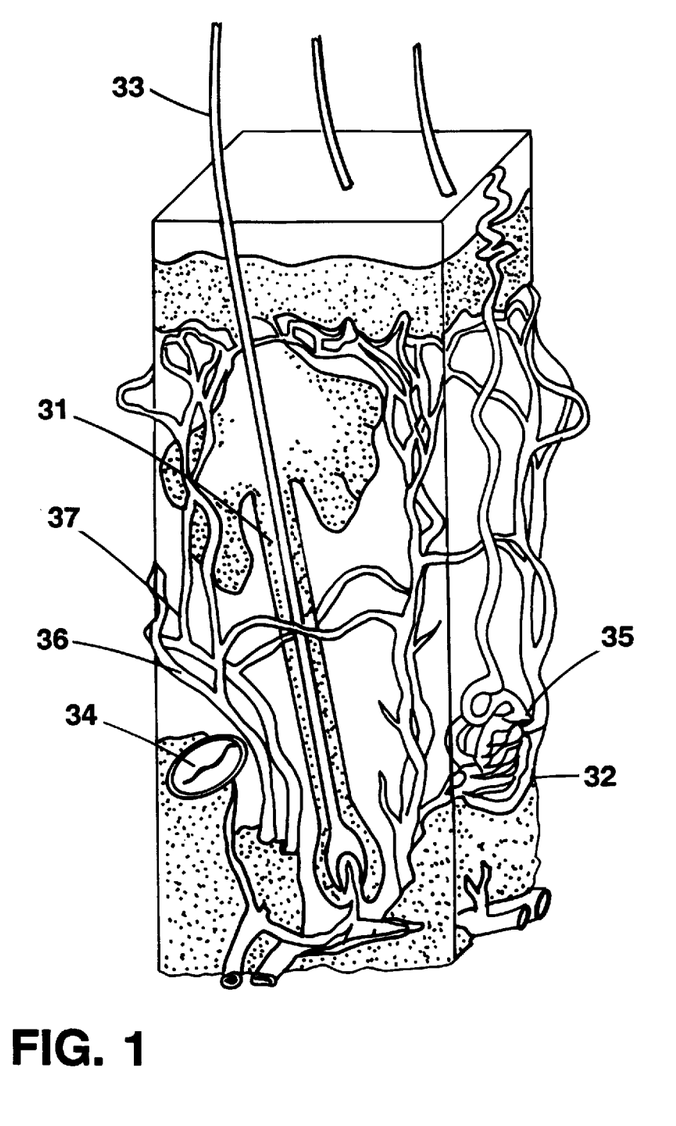
FIG. 1 is a drawing of a section of human skin showing a growing hair.

A section of human skin with a cross section of one hair is shown in FIG. 1. A first preferred embodiment of the present invention can be described by reference to FIGS. 2–4. FIG. 1 shows the hair shaft 33, a nerve ending 34, a sweat gland 35 and arteries 36 and veins 37. First, a laser absorbing carbon suspension is prepared of carbon powder in peach oil. The particle size of the powder preferably is about 10–20 nm and its concentration preferably is about 15% to 20% by volume.

Figure 2A:
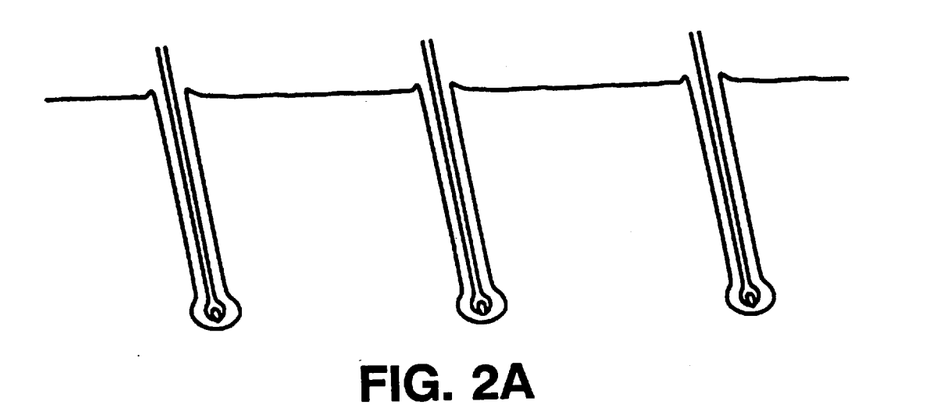
Figure 2B:
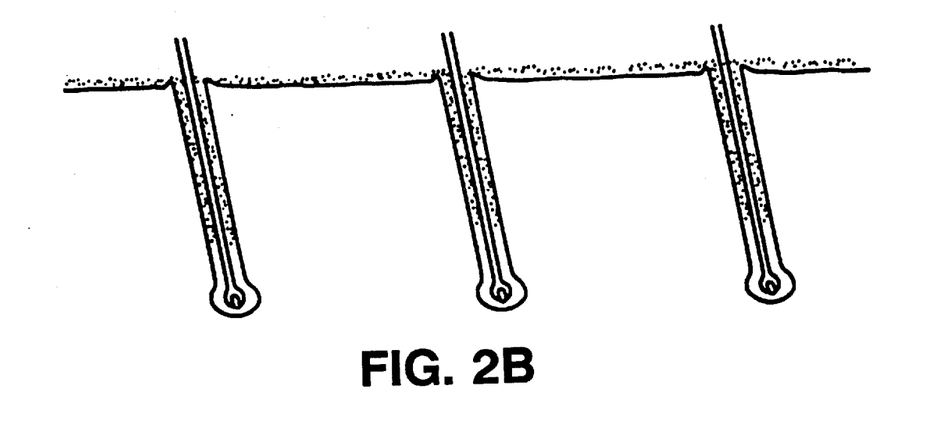
Figure 2C:
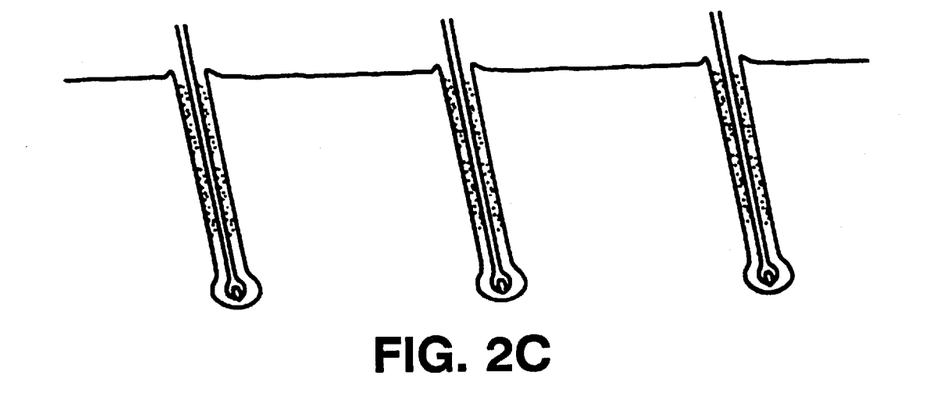

A clean section of skin is depicted in FIG. 2A. This suspension is rubbed on the skin with a massaging action so that a portion of the carbon suspension infiltrates the hair ducts of the hair that is to be removed as shown in FIG. 2B. Ultrasound with frequencies in the range of 3.5 to 10 MHZ at a power level of about 0.1 to 0.2 with 4 to 5 minutes could be used to help force the suspension into the ducts. Next the surface of the skin is cleaned preferably with an alcohol pad to make the skin surface clean but to leave the hair pores contaminated with the carbon suspension as shown in FIG. 2C.

Laser Application

The laser device used in this preferred embodiment is a $CO_2$ pulse laser which has the spikes in the range of 10.6 microns. Light in this range will pass through the outer layer of the surface of the skin and is readily absorbed in the carbon. Laser parameters, such as pulse width and repetition rate can be selected to best fit the skin and hair types of the patients. The parameters for two specific examples that have been utilized with good results for hair removal and inhibition of regrowth are shown in Table 1:

TABLE 1

Parameters Preferred.

| | First Example | Second Example |
|---|---|---|
| Pulse Width | 275 ns | 200 ns |
| Repetition Rate | 30 Hz | 8 Hz |
| Laser Spot Size | 1 cm$^2$ | 1 cm$^2$ |
| Energy per Pulse | 0.1 Joule | 0.2 Joule |
| Scanning Rate | 20 seconds per 10 cm$^2$ | 30 seconds per 10 cm$^2$ |

Each point on the skin receives illumination for about 2 seconds and each square centimeter receives about 6 Joules. Some of the light is reflected. Of the light which is not reflected a significant portion of the energy of each pulse is absorbed in the carbon.

Figure 3:
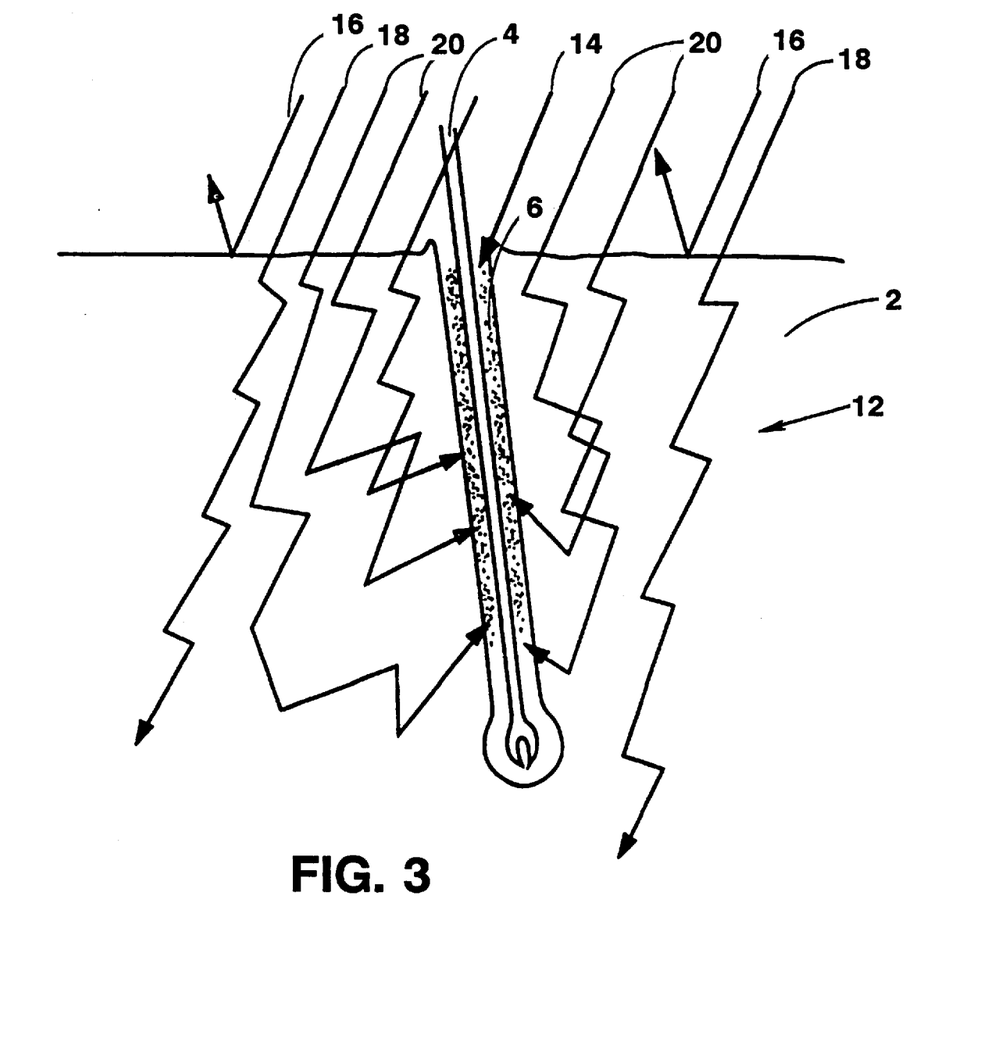
FIG. 3 shows qualitatively the paths of the photons of a laser pulse showing absorption in a carbon-oil suspension.

FIG. 3 shows a simplified view of a section of human skin and qualitatively the paths 12 of some of the photons of a laser pulse illuminating a section of skin 2 containing a hair duct with a hair 4 contaminated with carbon suspension 6. A few of the photons travel directly through the skin and are absorbed in the carbon (depicted by photon 14). Some are reflected from the skin surface (depicted by photons 16). Some are absorbed in the skin (depicted as photons 18) and a portion of the photons are absorbed in the carbon.

Operating within the parameters specified is important. They have been chosen to preferentially heat the carbon suspension which in turn heats the hair follicles and the blood vessels feeding the follicles to temperatures high enough to damage the hair follicles and/or the tissue feeding the follicles, but to minimize the heat to the rest of the skin tissue. The energy application time is a most important parameter. It must be chosen so that a large amount of energy is deposited in the suspension quickly so that the temperature of the suspension rises rapidly to about above 70°–80° C. This temperature applied for about 1 second is high enough to damage the follicles and/or the vessels feeding the follicles. During this short period heat transferred to the skin tissue is not enough to damage the skin tissue except that tissue immediately surrounding the follicle. A good practice is to start out with the power densities specified. It will be evident when enough energy is being supplied because the hair shaft will begin to curl. If curling is not achieved, the power density could be increased up to about 2–3 Joules per square centimeter, or until sufficient energy is delivered to effect long term inhibition of regrowth of a hair from the follicle.

Hair removal experiments have been performed using the parameters shown in Table 2 with excellent results. There is no significant pain. Regrowth of the hair is generally delayed for a period of from about 3 to about 5 months, and there is no apparent detrimental effect. In some cases regrowth of the treated hairs does not occur.

A qualitative mathematical analysis has been performed in order to estimate heat absorption and temperature distribution in the hair and skin tissue. This analysis is shown in Table 3.

Thus, under these assumptions each pulse would heat the carbon oil suspension roughly about 5° C. (The reader is cautioned that the above analysis is not to be relied on as a quantitative description of the process of heating the carbon oil suspension in the hair duct. For example, for many people the assumption that ¼ of the energy of each pulse goes into the hair duct is probably too high.)

Each pulse will also heat the skin in general. A good estimate is not available of the portions of the energy of the pulse reflected, absorbed in the hair ducts and absorbed in the skin in general. However, for this qualitative analysis, it was assumed that about ½ of the energy the laser pulse reflects, ¼ is absorbed in the hair ducts and ¼ is absorbed in the skin in general. If it is assumed that the skin is heated fairly uniformly to a depth of 0.2 cm, a skin density of 1 gm/cm$^3$ and a specific heat for the skin, of 4 J/gm°C., the 0.025 J pulse will heat this typical skin section about 0.04° C.

TABLE 2

Heating of hair and carbon oil suspension in hair ducts.

| | |
|---|---|
| Repetition Rate | 33 pulses per second |
| Time between pulses | about 0.03 seconds |
| Hair duct diameter | 0.1 mm |
| Energy per Pulse | 0.1 J |
| Energy per second | (0.1 J) (33) = 33 J/sec = 3 W |
| Beam spot | 1 cm$^2$ |
| Hair spacing | 130 hairs/cm$^2$ |
| Distance between hairs | 0.1 cm = 1 mm |
| Assume 1/4 of energy goes into a hair duct | |
| Energy per hair per pulse | (0.1 J/130)/4 = 0.00016 J |
| Volume of a hair duct | |
| Length | 1 mm |
| Diameter | 0.1 mm |
| Vol. = 1 π(D/2)$^2$ = | (0.1 cm) π (0.01/2)$^2$ = 0.0000078 cm$^3$ |
| Density of oil and hair = | 0.9 gm/cm$^3$ |
| Mass of oil & hair | 0.000007 gm |
| Specific heat of oil & hair assume | 4 J/gm °C. |
| Temperature rise per pulse, ΔT = Q/mc) | 0.00016 J / (0.000007 gm) 4 J/gm °C.) = 5° C. |

Based on these assumptions, the 60 pulses over about 2 seconds will give a general heating of about 2° C. Therefore, heat deposited generally to the skin would be negligible. (Again, the reader is cautioned regarding the qualitative nature of this analysis. In practice, much of the energy from the pulse $CO_2$ laser is absorbed in a very thin area of the surface possibly as thin as 0.1 mm depending on the dryness of the skin. In some cases a very thin layer of the skin is actually vaporized in the process, but this is usually the layer which consists of essentially dead cells which naturally flake off the skin surface. Also, since the epidermis is such a poor heat conductor the underlying layers of skin is typically protected from damaged except those portions very close to the carbon oil suspension.)

However, heat from the hot carbon oil suspension will be transferred by conduction to the tissue surrounding the hair duct. The following relationship was used to estimate the heat spread from the hot carbon oil suspension in the duct (see note 10 of Zwig & Wibber, IEEE Journal of Quantum Electronics, Vol. QE-23, No. 10 October (1987), Mechanical and Thermal Parameters In Pulsed Laser Cutting of Tissue):

$$\delta = \sqrt{K\tau}$$

where δ represents the thickness of a heated zone during a time τ, K being the heat of conduction. Assuming K=1.44× 10$^{-3}$ cm$^2$/S and using 0.03 sec as the time interval between pulses, it is estimated that the heat spreads out about 0.007 cm from the hair duct between each pulse. This is about equal to the radius of the hair duct so it is assumed that about one half of the temperature rise from each pulse is transferred to the surrounding tissue during the 0.03 second following each pulse. This means that the net increase in the temperature of the carbon-oil suspension from each pulse will be roughly 2.5° C.

Figure 4A:
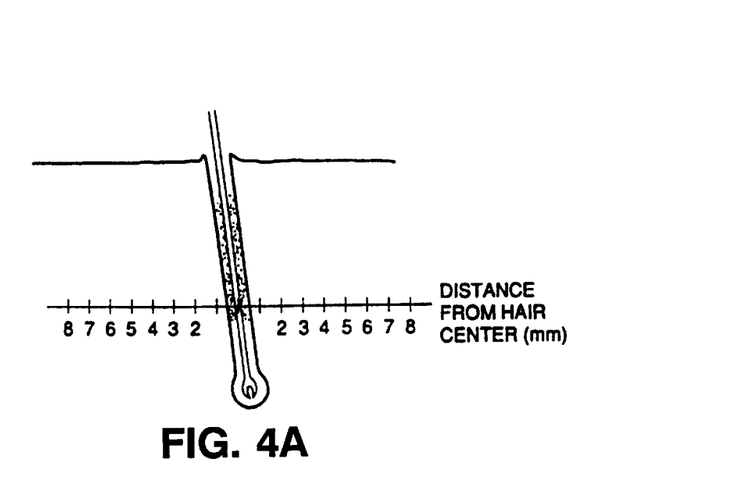
FIGS. 4A and B show the temperature distribution near a typical hair during the process of a preferred embodiment of the present invention.
Figure 4B:
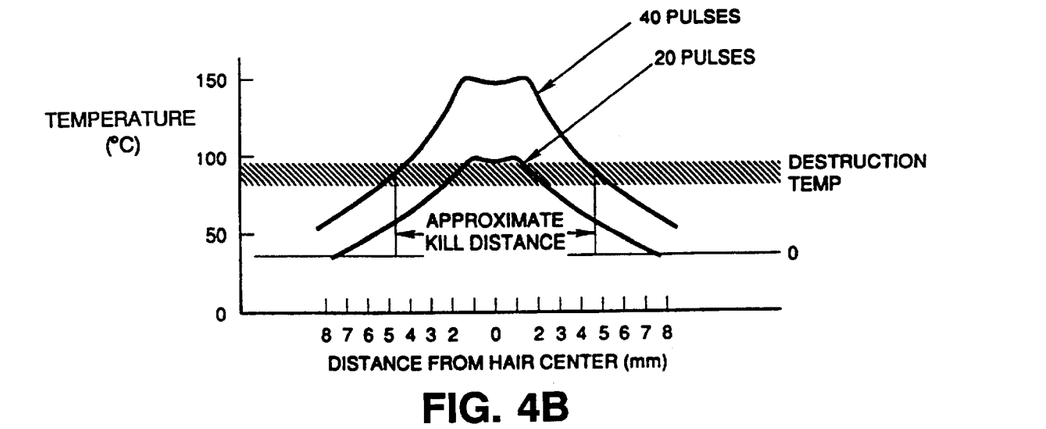

Thus, as depicted in FIG. 4 in about ⅔ second the temperature of the carbon-oil suspension in the hair duct has risen from a normal temperature of 37° C. to about 90° C., a temperature high enough to kill the follicle and the tissue cells immediately surrounding the hair follicle (i.e., within about ±5 hair diameters). In a little more than one second the temperature has risen to about 140° C. which is currently proposed as the upper range. At this point the patient would begin to feel pain. Therefore, the illumination should be applied so that no spot is illuminated longer than about one or two seconds during one scan. FIGS. 4A and 4B show a rough approximation of the temperature distribution between ±8 millimeters of the center for a typical hair duct after 20 and 40 pulses.

For this process, a 10 cm$^2$ area was illuminated by making 2 or 3 passes over each spot during a 20 second scanning period. For each spot the temperature will have dropped from the range of about 100°C.–140° C. to below about 50° C. during the approximately 7 seconds between scans.

As a result of the illumination, for many patients regrowth of hairs from the follicles does not recur for from about 3 to about 5 months because of reduced nourishment due to the destruction of the tissue surrounding the hair duct which feeds the follicle. It is estimated that the destroyed tissue is confined to within about 3–6, millimeters (about 6–12 hair diameters) of the center of the hair. In some cases pain and some surface burning is experienced before the hair tissue is destroyed. For these persons, hair regrowth can be inhibited by the use of one of the following alternative embodiments.

NEAR INFRARED LASER METHOD

This process is the same as the first embodiment described above except the laser wavelength is 1.06 microns, the pulse duration is about 1000 times less (i.e., in the range of 25–30 picoseconds), the energy per pulse is about 100 times less or about 3–6 mJ, and the spot size is about 0.1 to 0.3 cm$^2$. At this wavelength the skin penetration is maximum. In this case much less energy is required because a much larger percentage of the energy is absorbed in the contaminant.

STAIN METHOD

Figure 5:
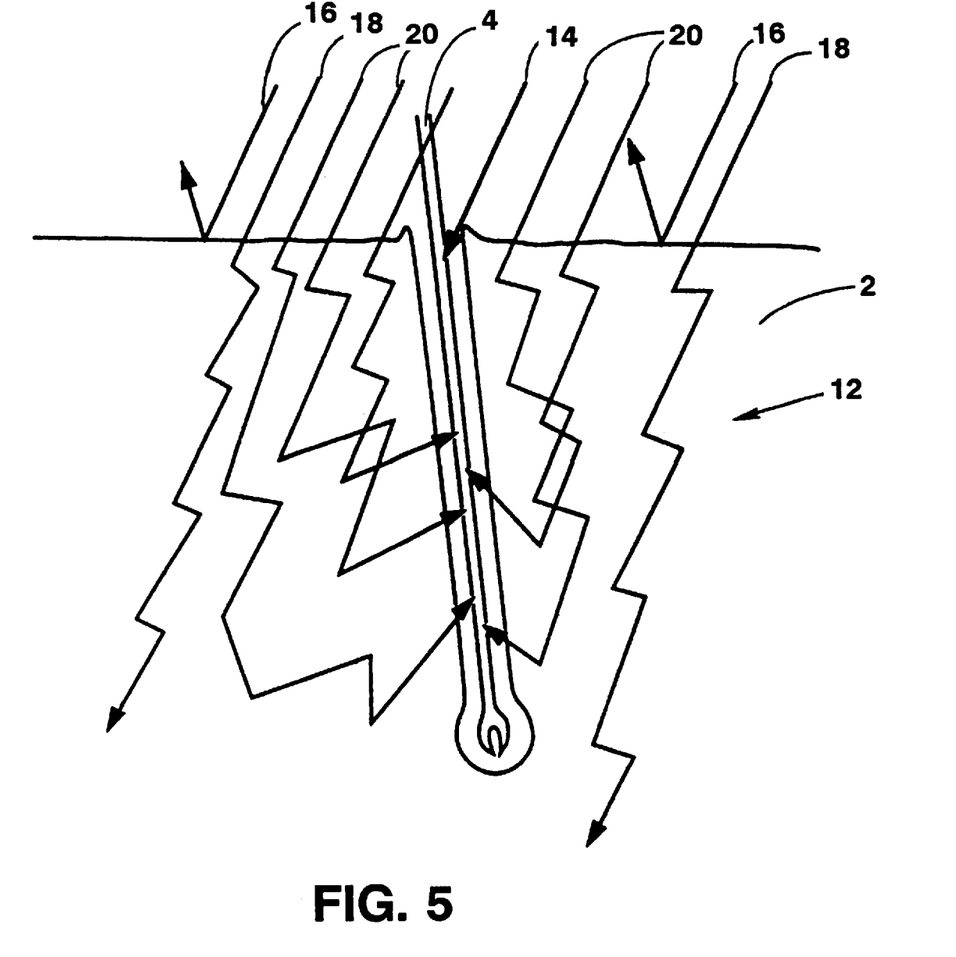
FIG. 5 shows qualitatively the paths of the photons of a laser pulse showing absorption in hair dye.

A second embodiment involves the use of dyes to stain the hair follicles. A pulse laser beam of light having a wavelength corresponding precisely to a resonance frequency of the dye illuminates the hair and skin area where the hair is to be removed. The dye and laser beam are chosen so that there is very little absorption by the skin tissue but great absorption by the dye. As indicated in FIG. 5 the photons will undergo diffuse reflection in the skin. But when a photon intersects the hair, it is absorbed.

To stain the follicles, dye is mixed to form a solution which will penetrate into the follicles. A good substance used to form this solution is hydropertis. In one embodiment, a commercial hair dye #124 (deep black with blue) or India ink, which already contains such a solution, was used. It is rubbed on the skin and hair and let stand for 30 minutes. The dye will migrate through the hair all the way to the root. India ink could also be used.

The skin is cleaned using standard dye removal solution. India ink and dye #124 have absorption peaks at ~694 nm and ~587 nm, which match perfectly with the wavelength of 587 nm dye laser. Dye #124 also has resonance peaks at 531 and 584 nm, which resonance peaks correspond to the output of a copper vapor laser supplied by Spectra Physics.

For this embodiment, a pulse width of 150 ns is supplied by a ruby laser or a 200 μs dye laser. With a beam cross sectional diameter of 0.4 cm, the energy density is 2.5–8.5 J/cm$^2$. There are many other dye-laser combinations available which will be obvious to persons skilled in the laser art. The secret is to match the laser wavelength with a resonance peak in a dye that can be applied to and absorbed in the follicles. India ink (essentially the same as tattoo ink) has high absorption peaks in a range from UV up to IR.

Described below is a good general procedure for hair removal practicing the stain method.

1. Discolor hairs with hydroperoxide 1 hour prior to staining hairs.
2. Cut or shave hairs leaving about 1 mm of hair above the skin.
3. Stain hairs with the ink or dye (red or orange, preferably). More ink or dye would be located around the hair and its pores because of the liquid surface tension near the hair.
4. Leave substance covered for 40–50 minutes.
5. Wash the skin surface several times with alcohol, until the skin surface returns to its normal color, except hair pores.
6. Make 3–4 spots for the test with different power densities to choose an individual optimal dose for the patient.
7. Start lasing 3–6 hours after the staining procedure, one laser shot per spot.
8. Cover the area irradiated with Aloe Vera Gel or Laser Cream after the procedure.
9. Give these instructions to the patient:
 use Bicitraine ointment topically for the first three days;
 spare the area irradiated when taking shower, don't use hard sponges;
 protect the area from direct sunlight by sunscreen or dress;
 take Tylenol® tablets if there is any discomfort;
 call if necessary.
10. Examine the skin after 1, 2, and 3 weeks.
11. Repeat the procedure if necessary for the hairs which were in anagen or catagen phases during the laser hair removal.

A titanium-sapphire laser could be used. This laser covers the parameters of a ruby laser, penetrates human skin about as well as a ruby laser, and has a wider band of radiation within the absorption spectrum of these dyes.

PHOTO CHEMICAL DESTRUCTION

A third embodiment for practicing this invention is to apply a photosensitizer to the hair, for example, so that it is absorbed along the full length of the hair duct to the root. The skin area containing the contaminated hairs is then illuminated with laser light that readily penetrates the skin without substantial absorption, but is absorbed resonantly by the photosensitizer. Hair-producing cells that are nearby or adjacent to the hair duct and papilla that are in the phase of the hair growth cycle characterized by rapid growth have very rapid metabolism (second only to tumor cells). These cells preferentially absorb the photosensitizer within minutes of its introduction to the hair duct. Upon irradiation with light at a resonant frequency, the photosensitizer undergoes a chemical reaction that damages the cells into which it has been absorbed. Hematoporphyrin derivatives, for instance, produce singlet oxygen upon illumination with laser light at a resonant frequency. Since the photosensitizer is preferentially absorbed into the cells responsible for hair growth, irradiation of the treated skin section with light at a resonant frequency of the photosensitizer will preferentially damage the hair producing cells.

To take advantage of the rapid, preferential absorption of the photosensitizer by the rapidly proliferating hair-producing cells, lasing should commence soon after absorption of the photosensitizer by the rapidly proliferating hair-producing cells, and before the photosensitizer is deposited into more slowly proliferating cells, whose destruction is not sought. As a general rule, lasing should commence before the photosensitizer is taken up by cells proliferating at a more common rate. For this reason, in some cases lasing can commence as soon as about 20 minutes following topical administration of the photosensitizer to the hair ducts. Lasing should not be done more than about 24 hours after administration of the photosensitizer to avoid damage to cells proliferating at a common rate.

A good specific example of this embodiment of the invention is to apply a 20 percent by weight solution of a hematoporphryin derivative topically to a skin section from which the hair to be removed has been recently shaved. The solution is drawn into the hair duct by capillary action where it is preferentially absorbed by the rapidly proliferating cells at or near the hair duct and papilla surrounding the hair duct and/or into the portion of the hair remaining under the skin within the duct.

The topically treated skin area is illuminated with an argon dye laser at 632 nm. The energy required is about 5–10 Joules per square centimeter of skin surface. In this case, the period of irradiation is not very important. It could be several minutes per square centimeter. When the laser energy is selectively absorbed in the hematoporphyrin derivatives, singlet oxygen is produced as a result of photochemical reaction. As singlet oxygen is toxic for protein and phospholipids in cells in which it is generated, the follicles are sufficiently damaged to delay regrowth of hairs, generally for a period of some 3 to 5 months. In some cases hair regrowth is delayed indefinitely.

SKIN COVER METHOD

This method is essentially the same as the Coat and Heat Method described above except that the surface of the skin is not cleaned after the application of and massaging in of the carbon-oil suspension. Prior to irradiation, the skin surface appears as shown in cross-section in FIG. 2B, instead of as shown in FIG. 2C. In this case the carbon-oil suspension serves as a shield for the skin surface, permitting use of higher laser doses with no significant injury to the epidermis and dermis of the skin. Preliminary tests indicate that this is a very effective and safe method of hair removal. The outermost surface of the skin, being a very good insulator, prevents any substantial heat transfer to the lower layers of the skin, and prevents any significant damage to the skin.

ORAL AND INTRAVENOUS CONTAMINATION OF HAIR OF TISSUE

It is also possible to contaminate the hair or tissue feeding the hair by administering the contaminant orally or intravenously. A preferred method for oral contamination is as follows:

A solution of disodium fluorescein 2–5% concentration given orally. Within 3 to 72 hours a significant portion of the disodium fluoresein will be concentrated in the body hair of the patient. Sections of the skin containing the hair to be removed is irradiated with a laser pulsed at a wavelength matched to NaFl. Preferred laser sources are HeCd lasers (441 nm wavelength), Nd:YAG (1,064 nm wavelength) frequency shifted to about 532 nm, and Er:Glass (1.54 µs) lasers tripled to produce a wavelength of about 513 nm. Other sources with wavelengths from 370 nm to 520 nm would be satisfactory. Preferred power levels are between 5 to 15 J/cm$^2$ depending such factors as the depth of hair follicles in the skin section to be treated, skin type, and rate of metabolism of disodium fluoresein. In one embodiment, the pulse duration is 1 µs or less.

OTHER CONTAMINANT—LASER COMBINATIONS

There are many other chemicals which can be used in the stain method and the photochemical method. Table 3 lists some of these along with a corresponding recommended laser for the illumination.

OTHER EMBODIMENTS

It is very important for all of these embodiments and in other embodiments which will be apparent to persons skilled in the art that the light absorbing substances have a very high absorption coefficient at frequencies which pass readily through the surface of the human skin. An illumination source is matched to this frequency. The substance used can be one with a high resonance peak at the frequency or it can be one with a high broad absorption coefficient over a wide band continuing the illumination frequency. The important thing is to use a light of a frequency which defuses through the skin and has a relatively low absorption in the skin and to use an absorber for contaminating the hair which will provide very high absorption of the light. Persons skilled in the art will recognize that certain frequencies will be preferred for light skinned persons and other frequencies may be preferred for dark skinned persons. The preferred beam size is about 1 square centimeter but could be as large as about 5 square centimeters.

TABLE 3

Dyes and matching laser.

| DYE | LASER |
|---|---|
| Hematoporphyrin derivatives | Argon Dye (630 nm) |
| Indocyanine Green | Diode Laser (785 nm) |
| Microcyanine | Cooper Vapor (540) |
| Photophryin II | Argon Dye (630) |
| Chlorin -E6 | Dye (660) |
| Chlorophyll derivatives | Argon Dye (630) |
| Black Ink | Ruby Laser (694) |
| Any of the above dyes | Tunable titanium-sapphire |

While the above description contains many specifications, the reader should not construe these as limitations on the scope of the invention, buy merely as exemplifications of preferred embodiments thereof Those skilled in the art will envision many other possible variations are within its scope. Accordingly the reader is requested to determine the scope of the invention by the appended claims and their legal equivalents, and not by the examples which have been given.

What is claimed is:

1. A process for inhibiting growth of hairs growing in hair ducts in a section of human skin comprising the steps of:

a. contaminating said hairs or tissue feeding said hairs with a photosensitizer having a high absorption at at least one frequency band of light, which photosensitizer is applied topically to said skin section, b. illuminating said skin section with said light at said at least one frequency band within about 20 minutes to about 2 hours following said contaminating so as to cause a chemical reaction to destroy tissue maintaining life of hairs growing in at least a plurality of said hair ducts.

2. The process as in claim 1 wherein said photosensitizer is a solution of hematoporphyrin derivatives.

3. The process as in claim 2 wherein said frequency band of light is provided by an argon dye laser at 632 nm.

4. The process as in claim 3 wherein said solution is an approximately 20% solution.

5. A process for inhibiting growth of hairs growing in hair ducts in a section of human skin comprising the steps of:

a. contaminating said hairs or tissue feeding said hairs with a photosensitizer having a high absorption at at least one frequency band of light;

b. illuminating said skin section with said light at said at least one frequency band within about 3 to about 6 hours following said contaminating so as to cause a chemical reaction to destroy tissue maintaining life of hairs growing in at least a plurality of said hair ducts.

6. The process as in claim 5 wherein the contaminant is applied by oral ingestion.

7. The process as in claim 6 wherein said photosensitizer is a solution of disodium fluorescein.

8. The process as in claim 7 wherein said solution is at a concentration of about 2–5%.

9. The process as in claim 8 wherein said frequency band of light is provided by a Nd:YAG laser frequency shifted to about 532 nm.

10. The process as in claim 8 wherein said frequency band of light is provided by a HeCd laser.

11. The process as in claim 5 wherein the contaminant is applied intravenously.

12. The process as in claim 1 or 5 wherein said at least one frequency band is not readily absorbed in skin.

13. The process as in claim 1 or 5 wherein said frequency band of light is provided by a Er:Glass laser tripled to a wavelength of about 513 nm.

14. The process as in claim 1 or 5 wherein said frequency band of light is provided by a laser.

15. The process as in claim 14 wherein said laser produces light pulses having a pulse duration less than or equal to about 1 µs.

16. The process as in claim 14 wherein said laser produces a beam size of about 1 $cm^2$ to about 5 $cm^2$.

17. The process as in claim 14 wherein said laser has a power level of about 5 $J/cm^2$ to about 15 $J/cm^2$.

* * * * *